(12) United States Patent
Galeotti et al.

(10) Patent No.: US 9,783,466 B2
(45) Date of Patent: Oct. 10, 2017

(54) ETHYLBENZENE DEHYDROGENATION PLANT FOR PRODUCING STYRENE AND RELATIVE PROCESS

(71) Applicant: VERSALIS S.P.A., San Donato Milanese (MI) (IT)

(72) Inventors: Armando Galeotti, Gonzaga (IT); Mirko Oliosi, Castelnuovo Del Garda (IT)

(73) Assignee: Versalis S.p.A., San Donato Milanese (IT)

( * ) Notice: Subject to any disclaimer, the term of this patent is extended or adjusted under 35 U.S.C. 154(b) by 0 days.

(21) Appl. No.: 15/035,600

(22) PCT Filed: Nov. 10, 2014

(86) PCT No.: PCT/IB2014/065916
§ 371 (c)(1),
(2) Date: May 10, 2016

(87) PCT Pub. No.: WO2015/068138
PCT Pub. Date: May 14, 2015

(65) Prior Publication Data
US 2016/0264496 A1    Sep. 15, 2016

(30) Foreign Application Priority Data
Nov. 11, 2013   (IT) .............................. MI2013A1870

(51) Int. Cl.
*B01J 8/04*          (2006.01)
*C07C 5/32*          (2006.01)
(Continued)

(52) U.S. Cl.
CPC ............... *C07C 5/333* (2013.01); *B01J 8/001* (2013.01); *B01J 19/24* (2013.01);
(Continued)

(58) Field of Classification Search
CPC .. B01J 8/04; B01J 8/0496; B01J 2208/00176; B01J 2208/00256; C07C 5/32; C07C 5/327
(Continued)

(56) References Cited

U.S. PATENT DOCUMENTS 3,417,156 A    12/1968  Berger
5,053,572 A    10/1991  Kim et al.
(Continued)

FOREIGN PATENT DOCUMENTS

CN    102040466 A    5/2011
CN    102503762 A    6/2012

OTHER PUBLICATIONS

International Search Report issued Feb. 16, 2016 in PCT/IB2014/065916.
(Continued)

*Primary Examiner* — Thuan D Dang
(74) *Attorney, Agent, or Firm* — Oblon, McClelland, Maier & Neustadt, L.L.P.

(57) ABSTRACT

An ethylbenzene dehydrogenation plant for producing styrene which comprises a reaction section in which one or more adiabatic reaction apparatuses are positioned in series, and a steam circuit in which there is at least one first steam heat exchange apparatus; said plant being characterized in that it comprises heating equipment in which there is a heating circuit by means of recirculation of the fumes formed during dehydrogenation processes of ethylbenzene to give styrene, wherein said heating equipment comprises the following apparatuses in fluid communication with each other by means of said heating circuit: one or more ultra-heating apparatuses, one or more combustion devices in which at least one steam diffuser, one burner and at least one mixing apparatus are inserted, one or more ventilation device(s).

13 Claims, 6 Drawing Sheets

(51) Int. Cl.
   *C07C 5/327* (2006.01)
   *C07C 5/333* (2006.01)
   *B01J 8/00* (2006.01)
   *B01J 19/24* (2006.01)

(52) U.S. Cl.
   CPC ............ *B01J 2208/00176* (2013.01); *B01J 2208/00256* (2013.01); *B01J 2208/00265* (2013.01); *B01J 2208/00504* (2013.01); *B01J 2219/00024* (2013.01); *B01J 2219/00103* (2013.01)

(58) Field of Classification Search
   USPC ........ 422/631, 643, 649, 198, 109; 585/440, 585/441
   See application file for complete search history.

(56) References Cited

U.S. PATENT DOCUMENTS

| | | |
|---|---|---|
| 2009/0264692 A1 | 10/2009 | Welch et al. |
| 2012/0078025 A1 | 3/2012 | Welch et al. |

OTHER PUBLICATIONS

Combined Chinese Office Action and Search Report issued Nov. 30, 2016 in Chinese Patent Application No. 201480069566.8 (with English language translation).

STATE OF THE ART

ETHYLBENZENE DEHYDROGENATION PLANT FOR PRODUCING STYRENE AND RELATIVE PROCESS

The present invention relates to an ethylbenzene dehydrogenation plant for producing styrene and the relative process.

In the present patent application, all the operating conditions appearing in the text should be intended as being preferred conditions, even if not expressly declared.

For the purposes of the present description, the term "comprises" or "includes" also comprises the term "consist in" or "essentially consisting of".

For the purposes of the present description, the definitions of the ranges always include the extremes, unless otherwise specified.

The strong increase in the cost of energy that has been registered over recent years has had a significant impact on the production cost of styrene in the dehydrogenation process of ethylbenzene. This process, in fact, consumes a high quantity of energy, mainly in the form of steam. The processes currently available on the market, which are licensed by Lummus, Badger LLC and Versalis are very similar and are all based on a first dehydrogenation phase of ethylbenzene, carried out in two or three adiabatic reaction steps, followed by a distillation phase. Almost 80% of the approximate million tons of styrene produced worldwide, is obtained through these technologies (Perp 07/08-4 Report Nexant Chem Systems Ethylbenzene/Styrene page 14).

The adiabatic dehydrogenation takes place at a high temperature and low pressure, in the presence of a large quantity of steam. Steam is fundamental for providing the reaction heat, as the dehydrogenation reaction is highly endothermic and also has the function of preserving the catalyst which, as a result of the cracking reactions, would otherwise be covered by coke and become inactive.

Over the last years, under the pressure of the demand for continuously improving the energy efficiency of dehydrogenation plants of ethylbenzene, producers of catalysts (such as Sud Chemie and BASF, for example) have developed increasingly stable catalysts also in the presence of increasingly reduced quantities of steam (partial pressure). Values ranging from 8-9 moles of $H_2O$ per mole of ethylbenzene (corresponding to a weight ratio of 1.36-1.53 of kg of water per kg of ethylbenzene) have passed to values lower than 6 moles of $H_2O$ for each mole of ethylbenzene (corresponding to 1 kg of water per kg of ethylbenzene) significantly reducing the consumption of steam in the dehydrogenation phase and increasing the overall energy efficiency of the process.

In order to operate with reduced quantities of steam, however, it is necessary to significantly increase the temperature of the steam, which is not always possible to perform, above all in existing plants, due to the temperature limits allowed for the construction materials available. As a result of the limits of use of the materials available in the pipes and equipment of existing plants, it is not possible to exceed 900° C., whereas in the radiant tubes of the steam superheating furnace, which have smaller dimensions, it is not possible to exceed 1100° C.

Under normal operating conditions in existing plants, these temperature values can be lower and reach 800° C. in the pipes and equipment, and 980° C. in the radiant tubes.

In other words, in the past, in order to be stable, i.e. not to be covered with coke, in the reaction environment, thus becoming inert, the catalysts required a large quantity of steam and consequently, in the presence of a large quantity of steam, there was no problem of supplying the heat necessary for the reaction.

Today, on the other hand, the catalysts require much less steam, and in order to supply the same heat, said steam must be heated to temperatures which are so high as to become critical for the materials.

US 2009/264692 discloses a method for increasing the efficiency and/or expanding the capacity of a new and existing dehydrogenation unit, comprising the steps:
 providing at least one dehydrogenation reactor and a feed stream,
 adding at least one direct heating unit (DHU) to a new or existing dehydrogenation unit having a reheater, whereby the DHU and reheater are positioned before or after at least one reactor, and wherein the DHU and the reheater are operated in parallel arrangement with respect to each other;
 diverting between 0.5% and 85% of a reactor effluent from the reactor to the DHU for heating and feeding the remainder of the reactor effluent to the reheater for heating;
 feeding the heated streams from the DHU and the reheater to a subsequent reactor, wherein there is an energy savings for operating the new or existing dehydrogenation unit with an added DHU as compared to operating a dehydrogenation unit with only a reheater and no added DHU.

There is therefore the necessity of overcoming the constraint due to the conflict between the requirement of ensuring, through steam, the necessary heat supply for the endothermic dehydrogenation reaction of ethylbenzene and the increasingly reduced quantity of steam due to the development of alternative catalysts, necessary for ensuring the stability of the catalyst.

In order to overcome these critical aspects mentioned above, the Applicant has found a new plant configuration for production processes of styrene via the dehydrogenation of ethylbenzene. This new plant provides the installation of a heating apparatus which exploits the fumes generated in the process, as thermal vector, allowing them to circulate in a suitable heating circuit.

The fumes circulating in this apparatus can be those produced inside a combustion device.

The fumes contain purging gases, hydrocarbons and water and the concentration of water ranges from 10 to 70% by volume.

In addition, the Applicant also proposes a new process for the dehydrogenation of ethylbenzene to give styrene wherein the fumes formed during the same process never exceed the temperature of 800° C.

The present invention therefore relates to a dehydrogenation plant of ethylbenzene to produce styrene which comprises a reaction section in which one or more adiabatic reaction apparatuses are positioned in series, and a steam circuit in which there is at least one first steam heat exchange apparatus; said plant being characterized in that it comprises a heating apparatus in which there is a heating circuit by means of recirculation of the fumes formed during dehydrogenation processes of ethylbenzene to give styrene, wherein said heating apparatus comprises the following apparatuses in fluid communication with each other by means of said heating circuit:
 one or more ultra-heating apparatuses,
 one or more combustion devices in which at least one steam diffuser, at least one burner and at least one mixing apparatus are inserted, one or more ventilation devices.

In a second embodiment, the present invention relates to a process for the dehydrogenation of ethylbenzene to produce styrene which comprises the following steps:

a. reacting a mixture of reagents containing steam and ethylbenzene, in the presence of a catalyst, in one or more adiabatic reaction steps in series, preferably at least two steps in series, more preferably two steps, b. circulating steam so that it transfers at least a part of its sensitive heat to the reagents or to the intermediate reaction products in the numerous reaction steps, c. heating a stream of fumes to a temperature lower than 800° C. and recirculating said fumes so that they transfer their sensitive heat to the reagents, or to the intermediate reaction products generated during the numerous reaction steps, or to the steam necessary for effecting the dehydrogenation, or a combination thereof.

The insertion of a specific heating apparatus having a heating circuit by the recirculation of fumes can be effected either on existing plants or on newly constructed plants.

Both in the case of an existing plant and of a newly constructed plant, benefit can be obtained from a decrease in the maximum temperature at which the steam leaving the furnaces must be heated. This benefit consists in being able to use a different material which is less expensive, easier to process and which can be supplied more rapidly or, with the same material, in the possibility of using a more reduced thickness in the construction materials with benefits relating to the operating reliability. More reduced thicknesses cause lower gradients during transients especially in cases of upsets. Lower temperature gradients correspond to lower internal stresses in the piping elements and equipment.

Dehydrogenation processes have been developed in the past, using combustion fumes as thermal vector. The fumes, however, have a very low heat capacity and consequently in order to have an adequate heat exchange at temperatures sufficiently low as to allow the use of conventional metallic materials, an extremely high flow-rate of fumes was necessary, which was then discharged to the stacks making the process less efficient.

The invention, object of the present patent application, on the other hand, envisages a heating apparatus in which a significant proportion of the fumes generated in the dehydrogenation process, in particular those generated in a combustion device, is recirculated. The flow-rate of fumes circulating must be very high so that the heating apparatus can operate with modest temperature ranges.

Furthermore, according to preferred embodiments of the present invention, steam can be added to the fumes up to a concentration equal to 50% by volume, which, having a specific heat which is double with respect to the fumes, makes it possible to operate with much lower temperature ranges, with an equal heat transfer.

By recycling the fumes, the specific heat can be significantly modified, also adding a small amount of steam. If the fumes were not recirculated, in order to obtain the same effect in terms of exchanged heat, a large quantity, of vapour would have to be added, resulting in a process which, on the whole, does not save vapour.

Thanks to the technical solution proposed by the Applicant, a part of the heat necessary for a dehydrogenation process of ethylbenzene can be provided by means of steam, in a quantity which is strictly indispensable for ensuring the stability of the catalyst, and a part of the heat by the circulation of the process fumes.

The high recycling flow-rates of fumes allow the plant to be maintained at a thermal level which is sufficiently low as to allow the use of conventional materials having a relatively low cost and which can be easily processed and supplied (such as, for example, stainless steel 304 H).

This system could also allow the yield to be increased in an existing plant without having to resort to costly revamping interventions on the steam circuit which is at an extremely high temperature.

Further objectives and advantages of the present invention will appear more evident from the following description and enclosed figures, provided for purely illustrative and non-limiting, purposes.

Figure 1:
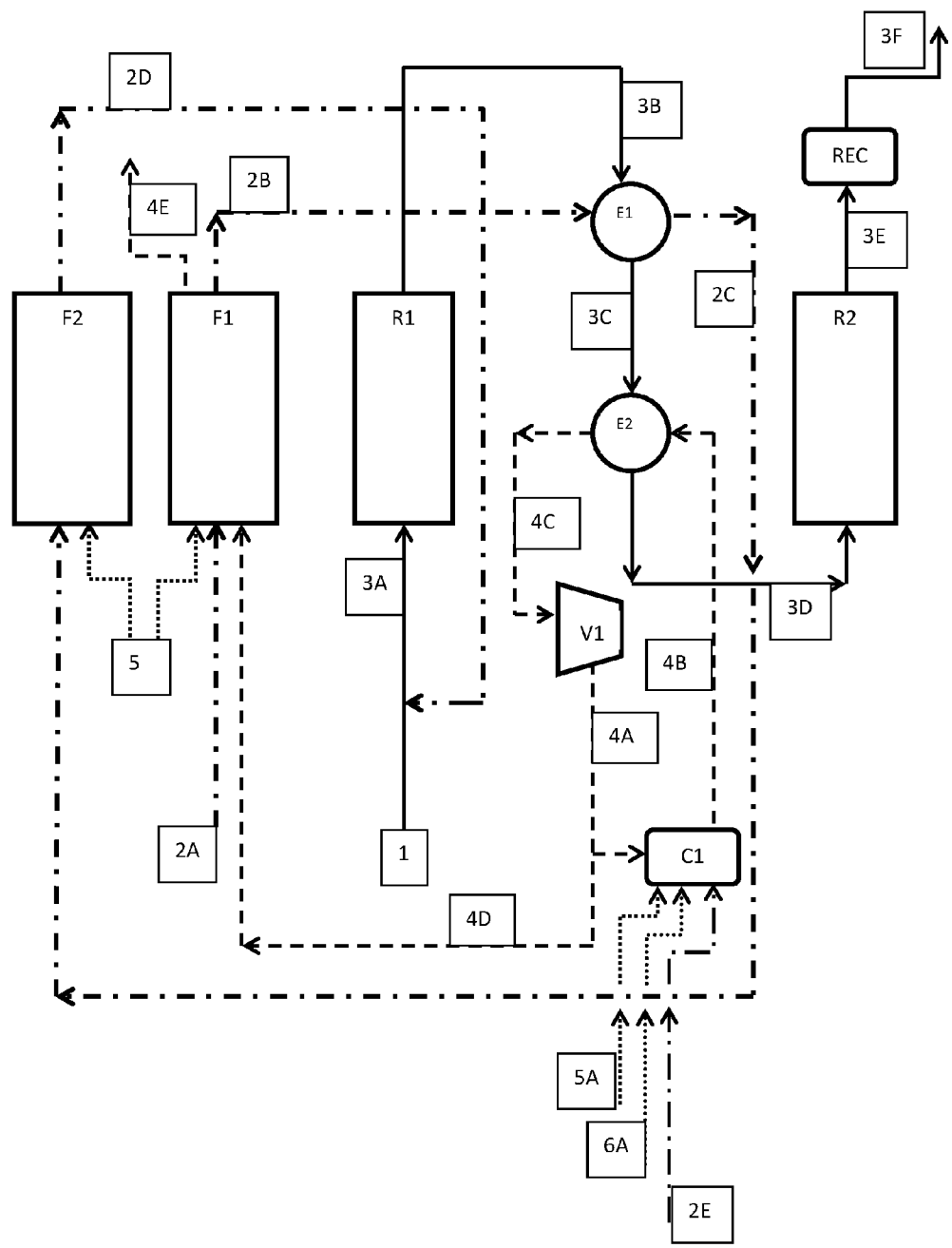
FIG. 1 is a block diagram of a dehydrogenation plant of ethylbenzene for producing styrene with two adiabatic reaction apparatuses in series, a heating apparatus and a heating circuit of the process fumes with a single ultra-heater according to the present invention.

The symbols used in the figures are explained hereunder.

F1 and F2 are two steam superheating furnaces for, or each a part of a furnace.

R1 and R2 are two adiabatic reaction apparatuses.

E1 is a steam heat exchange apparatus.

E2 is an ultra-heater.

E2A is a first ultra-heater and E2B is a second ultra-heater.

V1 is a ventilation device.

C1 is a combustion device.

X1 is a burner.

X2 is a vapour diffuser.

X3 is a mixing device.

REC is a recovery section of the heat from the products leaving the last reactor. REC can comprise some heat exchange apparatuses where steam is generated and/or steam, or a mixture of ethylbenzene and steam, is superheated.

The numerical indications 100, 200, 300, 400, 500 and 600 are the points in which the heating apparatus with a heating circuit of the fumes can be installed.

(1) is the ethylbenzene feedstock. (2A), (2B), (2C), (2D) and (2E) are steam streams, (3A) is a mixture of ethylbenzene and steam, (3B), (3C), (3D) the intermediate reaction product at different temperatures, (3E) and (3F) are the final products, (4A), (4B), (4C) and (4D) are streams of fumes, (4E) are the fumes from F, (5) and (5A) is natural gas, (6A) is air.

DETAILED DESCRIPTION

The Applicant will now describe an embodiment according to the present invention in detail, referring to FIGS. 1-5.

An object of the present invention relates to a dehydrogenation plant of ethylbenzene for producing styrene which comprises a reaction section in which one or more adiabatic reaction apparatuses are positioned in series (R1 and R2), and a steam circuit in which there is at least one first steam heat exchange apparatus (E1); said plant being characterized in that it comprises a heating apparatus in which there is a heating circuit for the recirculation of the fumes formed during dehydrogenation processes of ethylbenzene to give styrene, in particular those formed in a combustion device C1, wherein said heating apparatus comprises the following apparatuses in fluid communication with each other by means of said heating circuit:

one or more ultra-heating apparatuses (E2, E2A and E2B),
one or more combustion devices (C1) in which at least one steam diffuser (X2), at least one burner (X1) and at least one mixing apparatus (X3) are inserted,
one or more ventilation devices (V1).

A further embodiment of the present invention relates to a process for the dehydrogenation of ethylbenzene to produce styrene which comprises the following steps:

a. reacting a mixture of reagents containing steam and ethylbenzene, in the presence of a catalyst, in one or more adiabatic reaction steps in series, preferably at least two steps in series, more preferably two steps,
b. circulating steam so that it transfers at least a part of its sensitive heat to the reagents or to the intermediate reaction products in the multiple reaction steps,
c. heating a stream of fumes to a temperature lower than 800° C. and recirculating said fumes so that they transfer their sensitive heat to the reagents, or to the intermediate reaction products generated during the multiple reaction steps, or to the steam necessary for effecting the dehydrogenation, or a combination thereof.

The fumes circulating in said apparatus can be those produced inside a combustion device C1, which can be joined with the discharge fumes produced during a dehydrogenation process of ethylbenzene to give styrene. The fumes contain vent gas, hydrocarbons and water and the concentration of water ranges form 10% to 70% by volume, preferably the water concentration ranges from 15% to 45% by volume.

The fumes are recirculated with a flow-rate ranging from 10,000 kg/h to 100,000 kg/h, preferably ranging from 50,000 kg/h to 80,000 kg/h.

Said process is preferably carried out in the dehydrogenation plant of ethylbenzene described and claimed in the present text.

The heating apparatus with a circuit of fumes can be positioned in different points in the plant described and claimed in the present text, preferably between an adiabatic reactor and a subsequent reactor (200 and 100), or preferably on the feeding line of the feedstock to the first of the adiabatic reactors in series before the introduction of water vapour to the reactor (300) or after said introduction (600). Alternatively said heating apparatus with the recycling of fumes can be positioned preferably along the steam circuit (400 and 500), more preferably at the inlet of a superheating furnace.

The ultra-heating apparatus (E2) is typically a shell and tube heat exchanger and can be positioned upstream or downstream of a steam heat-exchange device (E1 known as superheater or overheater) which is usually already present in ethylbenzene dehydrogenation plants.

The heating apparatus with a heating circuit of the fumes may preferably comprise at least one or more, preferably two or more ultra-heaters in series (E2A and E2B), even more preferably two. In these cases, the first ultra-heater can be positioned both upstream and downstream of the steam heating device (E1), whereas the subsequent ultra-heaters (E2B) are positioned upstream of the ventilation device (V1).

The fumes generated in the dehydrogenation process circulate in the lines which put V1, C1 and the ultra-heaters in fluid communication.

The ventilation device can be a centrifugal or axial ventilator suitable for conveying high-temperature gas. There can be numerous ventilation devices and can be positioned in parallel downstream of only one ultra-heater and upstream of only one combustion device.

Figure 2:
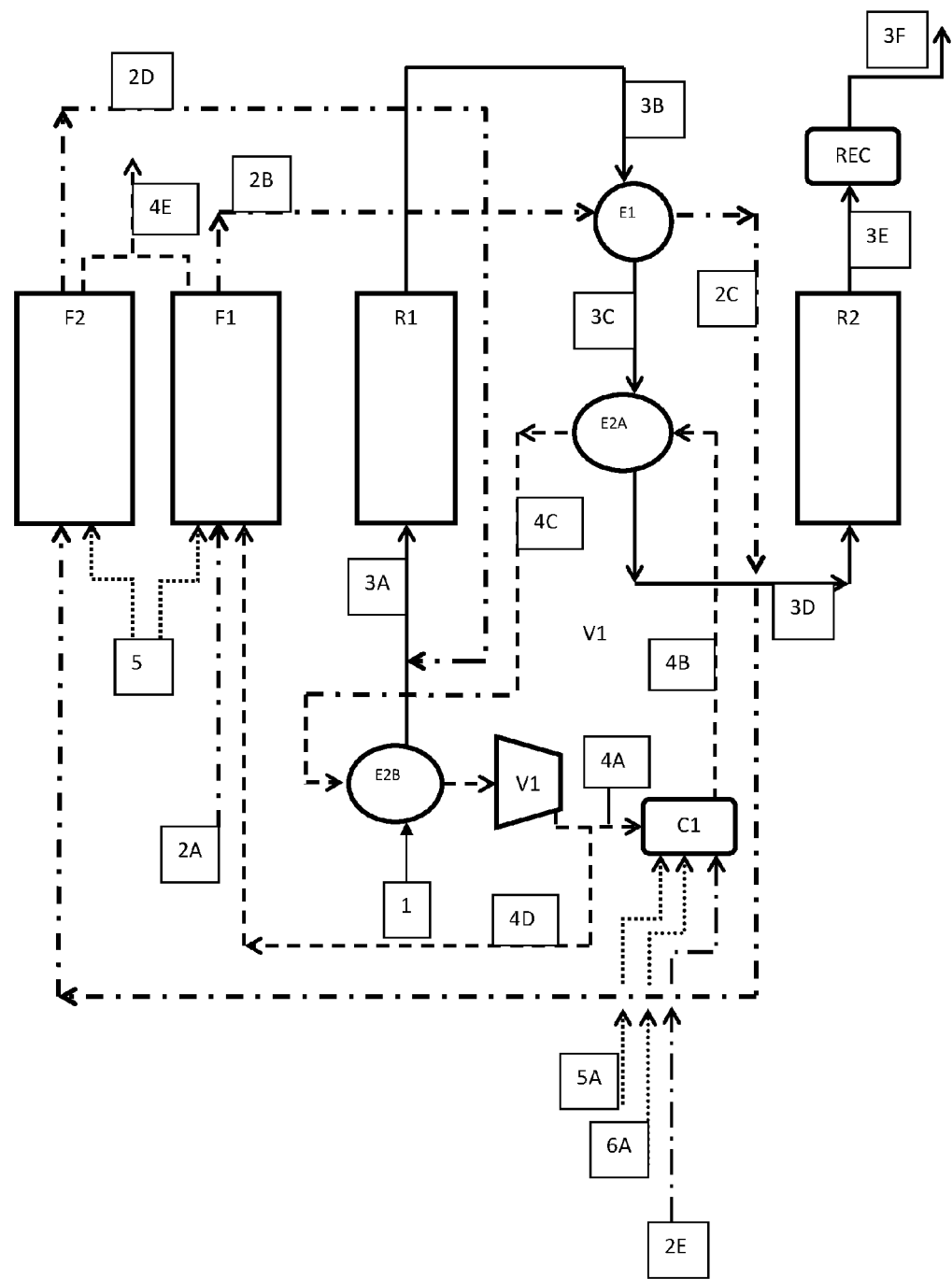
FIG. 2 is a block diagram of a dehydrogenation plant of ethylbenzene for producing styrene with two adiabatic reaction apparatuses in series, a heating apparatus and a heating circuit of the process fumes with a double ultra-heater according to the present invention.
Figure 3:
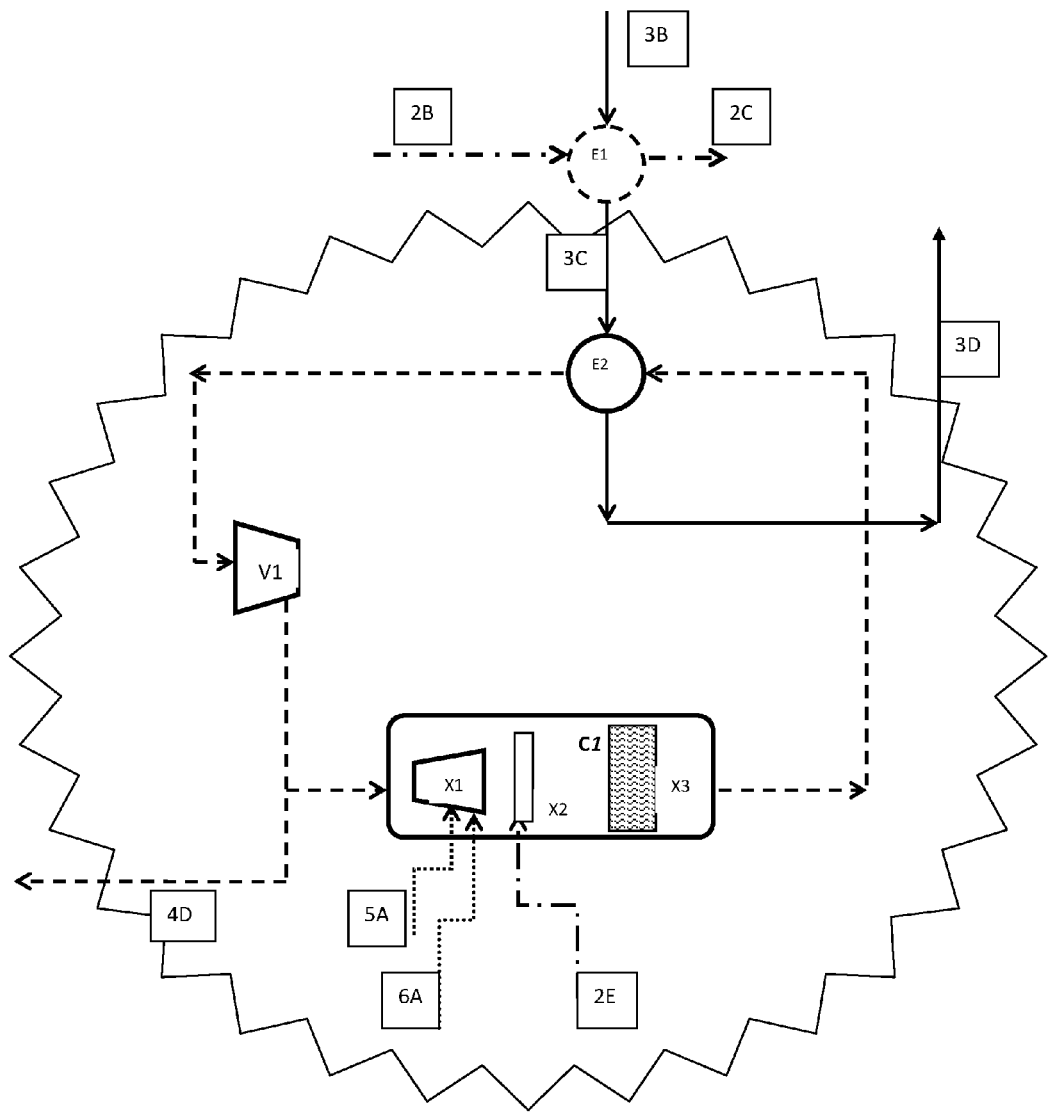
FIG. 3 is a block diagram of the heating apparatus with a heating circuit of the fumes and only one ultra-heater.
Figure 4:
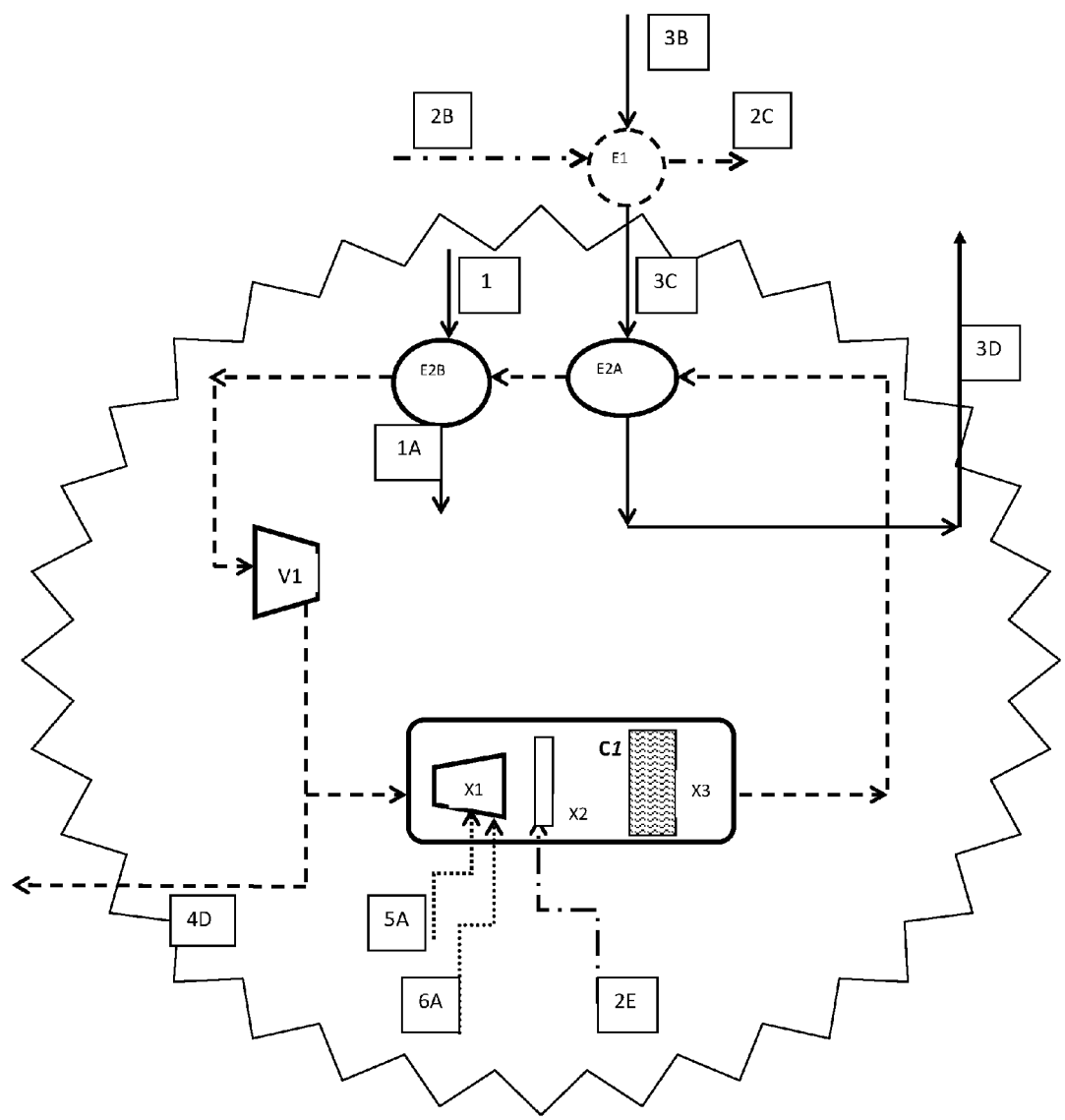
FIG. 4 is a block diagram of the heating apparatus with a heating circuit of the fumes and two ultra-heaters.
Figure 5:
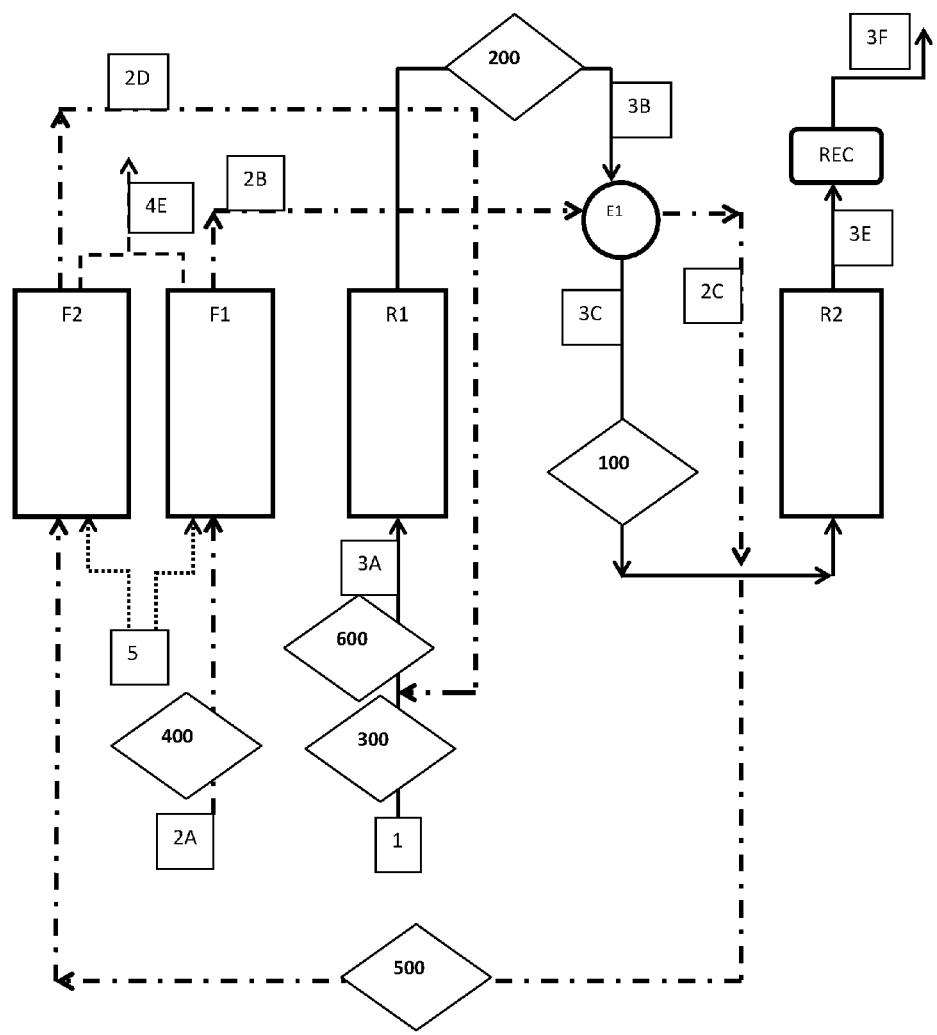
FIG. 5 is a block diagram of a dehydrogenation plant of ethylbenzene for producing styrene which indicates the positions in which the heating apparatus can be installed.

In order to describe the process in more detail, the Applicant will now refer to FIG. 1, and in the case of more than one ultra-heater, to FIG. 2.

A stream of ethylbenzene (1) is mixed with vapour (2D) and said mixture is fed to the first of the two reactors in series (R1). The intermediate product (3B), which contains a vent gas, hydrocarbons and water, is sent to a steam heat-exchange apparatus (E1) and subsequently to an ultra-heater apparatus (E2). The intermediate product leaving the ultra-heater then continues towards the subsequent reaction steps.

The intermediate product (3B) flows in the tubes of both the steam heat-exchange apparatus and in the tubes of the ultra-heater apparatus (E2). The steam (2B) coming from the superheating furnaces (F1) flows in the shell of the steam heat-exchange apparatus.

Vent gas relates to a mixture which includes hydrogen, carbon monoxide, carbon dioxide, nitrogen, oxygen, methane, ethane and ethylene, propane and propylene. Hydrocarbons refer to a mixture prevalently of aromatics with traces of paraffins and naphthenes, wherein the main components are styrene, ethylbenzene, toluene and benzene, preferably a mixture which comprises Ethylbenzene, Styrene, Toluene, Benzene, other $C_8$ and $C_9$ aromatics, Paraffins and naphthenes $C_6$-$C_8$.

The composition of the intermediate product comprises:
from 0% to 20% molar, preferably from 2 to 8%, of vent gas
from 5% to 25% molar, preferably from 5 to 15% molar, of hydrocarbons
from 70% to 90% molar, preferably from 75 to 85% molar, of water.

The intermediate product (3C) circulates in the tubes of the ultra-heater device and the temperature ranges from 400° C. to 700° C., preferably from 500° C. to 600° C., whereas the pressure ranges from 0 atm to 2 atm, preferably from 0.5 to 1.1 atm. The fumes (4B) circulate in the shell of said ultra-heater device.

The shell of the ultra-heater apparatus is fluidinamically connected to a circuit of fumes which are continuously recirculated with a flow-rate ranging from 10,000 kg/h to 100,000 kg/h, preferably from 50,000 kg/h to 80,000 kg/h. It is the ventilation device (V1) that creates the circulation of the process fumes in the heating circuit.

The circuit of fumes keeps the ventilation device (V1), the ultra-heater device (E2) and the combustion device (C1) in fluid communication.

The ventilation device (V1) sucks the fumes at the outlet (4C) of the ultra-heater apparatus (E2) at a pressure ranging from 0.5 atm to 1.5 atm, preferably from 0.9 to 1.2 atm, and a temperature ranging from 400° C. to 800° C., preferably from 550° C. to 750° C. A part of said fumes (4A) are sent from the ventilation device to a combustion device (C1) and a part (4D) to one of the superheating furnaces.

The fumes can be mixed with steam up to a concentration equal to 50% by volume, because, as it has double specific heat with respect to the fumes, it allows much lower temperature ranges to be used with the same heat transfer.

The circulation of fumes in the heating circuit can significantly modify the specific heat, also adding steam. If the fumes were not recirculated, a large quantity of vapour would have to be added in order to obtain the same effect in terms of exchanged heat, and the process would consequently, on the whole, not save vapour.

The combustion device (C1) comprises a burner in line (X1), preferably for gaseous fuel (for example a burner similar to those used in cogeneration units), which supplies heat by burning fuel gas (5A) with air (6A), and suitably increasing the temperature of the fumes which are sent back to the ultra-heater (4B) at a temperature ranging from 600° C. to 800° C., preferably from 650° C. to 750° C., more preferably from 700° C. to 750° C.

A water vapour diffuser (X2) and a mixing apparatus (X3) which mixes the combustion products coming from the burner (X1), the fumes coming from the ventilation device and the steam introduced by means of the steam diffuser (X2), are also present in the combustion device (C1). The flow-rate of the steam introduced through the steam diffuser is regulated by means of a specific device so as to keep the concentration of water in the recycled stream of hot gases at a value ranging from 10% to 70% by volume, preferably ranging from 15% to 45% by volume.

In order to keep the mass constant and therefore the pressure of the hot gases in the circuit of the heating apparatus described in the present text, at a value preferably ranging from 1 atm to 1.1 atm, part of the fumes in circulation (4D) are discharged by means of a pressure control device, sending them to a heat recovery system which can be specific for this stream, such as for example an economizer that generates and overheats low-pressure vapour, or it can be the same heat recovery system of the fumes of the steam superheating furnace (F1 or F2).

As previously indicated, there can be more than one, at least two, ultra-heaters, and they are positioned so that the intermediate reaction product (3B) flows in the tubes of the first ultra-heater of the series (E2A).

The ethylbenzene (1) and vapour fed to the first of the dehydrogenation reactors (R1) flow in the tubes of the second ultra-heater (E2B).

The shells of the first and second ultra-heater (E2A and E2B) are in fluid communication with the heating circuit of the fumes.

The heating apparatus can be advantageously applied on both existing ethylbenzene dehydrogenation plants and also on new plants.

When said apparatus is applied to an existing plant, it allows two objectives to be obtained:
a reduction in the consumption of vapour and/or
an increase in the plant capacity,
without having to revamp with costly substitutions of the furnaces and of the steam heating circuit. These objectives can be obtained individually or jointly.

In both cases, benefit can be obtained from a reduction in the maximum temperature to which the vapour leaving the furnaces must be heated. This benefit consists in being able to use a different material which is less expensive, easier to process and which can be supplied more rapidly or, with the same material, in the possibility of using a more reduced thickness with benefits relating to the operating reliability. More reduced thicknesses cause lower gradients during transients especially in cases of upsets. Lower temperature gradients correspond to lower internal stress in the piping elements and equipment.

EXAMPLES

The invention is better illustrated hereunder by some non-limiting embodiments of the objectives of the present patent application.

Example 1 describes a case of improvement in the energy consumption of an existing production plant of styrene via the dehydrogenation of ethylbenzene, in terms of a reduction in the consumption of steam.

As is known, this improvement can be obtained by significantly increasing the temperature of the steam which is overheated in the furnaces and sent through a specific circuit to a superheater installed between the two reactors. This temperature increase creates the necessity for costly modifications due to the partial reconstruction of the furnaces and reconstruction of the vapour circuit and superheater installed between the two reaction steps.

If, on the contrary, the heating apparatus with a heating circuit of the process fumes described in the present text is applied, the furnace, the superheater and also the vapour circuit can be preserved.

Thanks to the recycling of the fumes, heat can be supplied to the reaction mixture which passes from one reactor to another until the temperature is increased to over 640° C., maintaining the temperature of the thermal vector, the fumes, lower than 800° C. This limit corresponds to the limit allowed for use for the construction of pressurized equipment of some stainless steels of the austenitic type: among these, for example, the type 304 H, which has the best cost/performance ratio, but also 316H, 309H, 310H and 321H. These materials have been widely used in the past and are still mainly present as materials for the construction of equipment and lines in both existing styrene plants and in more modern plants. In more modern plants, alloys with a high Ni content having a much higher cost, with respect to austenitic steels, are widely used, which allow the operating temperature to be increased to over 800° C. and up to 900° C.

Also in the case of alloys with a high nickel content, however, it is in any case important to reduce the project temperature, which is linked to the maximum operating temperature, as this often causes a considerable reduction in the thickness of the materials used. In this respect, there is a decrease in the maximum operating temperature and consequently also the project temperature, of 50° C., as shown in Example 2, this decrease can be obtained by applying the device, object of the present invention. If the material is alloy 800 H, for example, and the project temperature (often higher than the operating temperature) is reduced from 925° C. to 875° C., the thickness can be reduced to ⅔. Considering the radiant tubes of the furnaces, which often use materials such as ASTM A608 grade HK40, by decreasing the project temperature from 1020° C., the limit allowed for this material, to 970° C., the thickness can be reduced to ¾.

In the examples, the gas comprises $H_2$, $CO_2$, $CO$, $N_2$, $O_2$, $CH_4$, $C_2H_6$, $C_2H_4$. The hydrocarbons include Ethylbenzene, Styrene, Toluene, Benzene, other $C_8$ and $C_9$ aromatics, Paraffins and naphthenes $C_6$-$C_8$.

The fumes leaving the two furnaces F1 and F2 are typically joined in a single stream in order to optimize the investment costs relating to the heat recovery system.

Comparative Example 1

Figure 6:
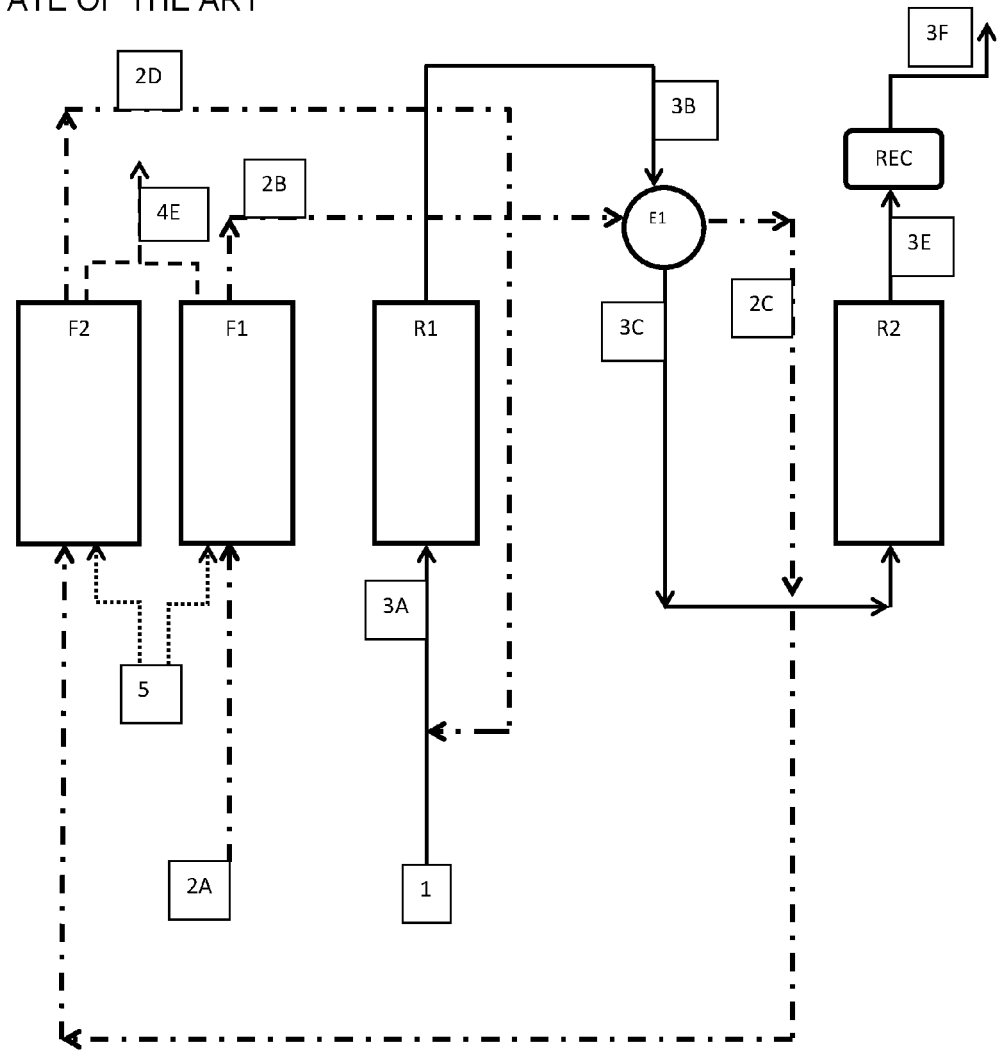
FIG. 6 is a dehydrogenation plant of ethylbenzene for producing styrene according to the known art.

The comparative example illustrates a plant for the dehydrogenation of ethylbenzene to produce styrene according to the state of the art. FIG. 6 illustrates two adiabatic reactors in series. The main working conditions are reported in Table 1. The conversion of ethylbenzene is 68% and the ratio between the steam and hydrocarbons is 1.4 kg/kg.

TABLE 1

(Referring to the scheme of FIG. 6).

| Stream | 1 | 2A | 2B | 2C | 2D | 3A |
|---|---|---|---|---|---|---|
| | Ethylbenzene feedstock | Steam fed | Steam from first furnace | Steam to second furnace | Steam to first reactor | Feeding to first reactor |
| Flow-rate [kg/h] | 89700 | 86730 | 86730 | 86730 | 86730 | 176427 |
| T [° C.] | 495 | 387 | 800 | 631 | 760 | 613 |
| Composition Vent Gas | 0% by wt | 0% by wt | 0% by wt | 0% by wt | 0% by wt | 0% by wt |
| Composition Hydrocarbons | 82% by wt | 0% by wt | 0% by wt | 0% by wt | 0% by wt | 42% by wt |
| Composition Water | 18% by wt | 100% by wt | 100% by wt | 100% by wt | 100% by wt | 58% by wt |

| Stream | 3B | 3C | 3E | 3F | 4E | 5 |
|---|---|---|---|---|---|---|
| | Outlet First Reactor | Feeding second reactor | Outlet second reactor | Reaction product | Fumes from furnaces | Natural Gas to furnaces |
| Flow-rate [kg/h] | 176427 | 176427 | 176427 | 176427 | 66200 | 3200 |
| T [° C.] | 538 | 619 | 563 | 174 | 150 | 25 |
| Composition Gas | 4.1% mol | 4.1% mol | 7.8% mol | 7.8% mol | 83% mol | 100% mol |
| Composition Hydrocarbons | 10.3% mol | 10.3% mol | 10% mol | 10% mol | 0% mol | 0% mol |
| Composition Water | 85.6% mol | 85.6% mol | 82.2% mol | 82.2% mol | 17% mol | 0% mol |

Comparative Example 1-A

Comparative example 1-A illustrates an existing plant for the dehydrogenation of ethylbenzene to produce styrene according to the state of the art, which uses a modern catalyst, stable also in the presence of a low partial water-vapour pressure, and operating with a steam/hydrocarbon ratio equal to 1.2 kg/kg with a conversion of ethylbenzene equal to 68%. The reference figure is again FIG. 6.

TABLE 1-A (Referring to the scheme of FIG. 6).

| Stream | 1 | 2A | 2B | 2C | 2D | 3A |
|---|---|---|---|---|---|---|
| Description | Ethylbenzene feedstock | Steam fed | Steam from first furnace | Steam to second furnace | Steam to first reactor | Feeding first reactor |
| Flow-rate [kg/h] | 89700 | 72030 | 72030 | 72030 | 72030 | 161730 |
| T [° C.] | 495 | 382 | 860 | 643 | 798 | 617 |
| Composition Vent Gas | 0% by wt | 0% by wt | 0% by wt | 0% by wt | 0% by wt | 0% by wt |
| Composition Hydrocarbons | 82% by wt | 0% by wt | 0% by wt | 0% by wt | 0% by wt | 45% by wt |
| Composition Water | 18% by wt | 100% by wt | 100% by wt | 100% by wt | 100% by wt | 55% by wt |

| Stream | 3B | 3C | 3E | 3F | 4E | 5 |
|---|---|---|---|---|---|---|
| Description | Outlet first reactor | Feeding second reactor | Outlet second reactor | Reaction product | Fumes from furnaces | Natural gas to furnaces |
| Flow-rate [kg/h] | 161730 | 161730 | 161730 | 161730 | 64500 | 3100 |
| T [° C.] | 536 | 629 | 568 | 162 | 150 | 25 |
| Composition Vent Gas | 5.5% mol | 5.5% mol | 8.9% mol | 8.9% mol | 83% mol | 100% mol |
| Composition Hydrocarbons | 11% mol | 11% mol | 11.3% mol | 11.3% mol | 0% mol | 0% mol |
| Com position Water | 83.5% mol | 83.5% mol | 79.8% mol | 79.8% mol | 17% mol | 0% mol |

Example 1

Example 1 illustrates the plant according to the scheme of FIG. 1, i.e. the present invention, which uses a modern catalyst, stable also in the presence of a low partial water-vapour pressure, and operating with a steam/hydrocarbon ratio equal to 1.2 kg/kg with a conversion of ethylbenzene equal to 68%, and including the heating apparatus which comprises the heating circuit of fumes.

Table 2 and Table 3 illustrate the working conditions of Example 1.

In this plant, which operates under the same conditions as Comparative Example 1-A, the advantage derives from the possibility of reaching the same inlet temperatures of the reactors, and therefore the same conversion of ethylbenzene, with lower temperatures of the heating circuits, in particular that of the steam leaving the furnaces. By maintaining the temperature at the outlet of the furnaces below 800° C., the same lines and equipment (furnaces F1, F2 and exchanger E1) can be preserved with benefits with respect to the time necessary for effecting the improvement operations and lower costs in addition to an easier supply of the materials.

TABLE 2

(Referring to the scheme of FIG. 1).

| Stream | 1 | 2A | 2B | 2C | 2D | 2E |
|---|---|---|---|---|---|---|
| Description | Ethylbenzene feedstock | Steam in feeding | Steam from first furnace | Steam to second furnace | Steam to first reactor | Steam to C1 |
| Flow-rate [kg/h] | 89700 | 72030 | 72030 | 72030 | 72030 | 700 |
| T [° C.] | 495 | 382 | 799 | 622 | 798 | 200 |
| Composition Vent Gas | 0% by wt | 0% by wt | 0% by wt | 0% by wt | 0% by wt | 0% by wt |
| Composition Hydrocarbons | 82% by wt | 0% by wt | 0% by wt | 0% by wt | 0% by wt | 0% by wt |
| Composition Water | 18% by wt | 100% by wt | 100% by wt | 100% by wt | 100% by wt | 100% by wt |

| Stream | 3A | 3B | 3C | 3D | 3E | 3F |
|---|---|---|---|---|---|---|
| Description | Feeding first reactor | Outlet first reactor | Feeding ultra-heater | Feeding Second reactor | Outlet second reactor | Reaction product |
| Flow-rate [kg/h] | 161730 | 161730 | 161730 | 161730 | 161730 | 161730 |
| T [° C.] | 617 | 536 | 612 | 629 | 568 | 162 |
| Composition Vent Gas | 0% by wt | 5.5% mol | 5.5% mol | 5.5% mol | 8.9% mol | 8.9% mol |
| Composition Hydrocarbons | 45% by wt | 11% mol | 11% mol | 11% mol | 11.3% mol | 11.3% mol |
| Composition Water | 55% by wt | 83.5% mol | 83.5% mol | 83.5% mol | 79.8% mol | 79.8% mol |

TABLE 3

(Referring to the scheme of FIG. 1).

| Stream | 4A | 4B | 4C | 4D | 4E |
|---|---|---|---|---|---|
| Description | Hot gases from V1 | Gas to ultra-heater | Gas from ultra-heater | Hot Gases to furnaces | Fumes from furnaces |
| Flow-rate [kg/h] | 76000 | 76000 | 76000 | 5260 | 65150 |
| T [° C.] | 727 | 790 | 727 | 727 | 150 |
| Composition Vent Gas | 70% vol | 70% vol | 70% vol | 70% vol | 82% vol |
| Composition Hydrocarbons | 0% vol | 0% vol | 0% vol | 0% vol | 0% vol |
| Composition Water | 30% vol | 30% vol | 30% vol | 30% vol | 18% vol |

| Stream | 5 | 5A | 6A |
|---|---|---|---|
| Description | Natural Gas to furnaces | Gas to C1 | Combustion Air to C1 |
| Flow-rate [kg/h] | 2900 | 210 | 4350 |
| T [° C.] | 25 | 25 | 25 |
| Composition Vent Gas | 100% mol | 100% mol | 100% mol |
| Composition Hydrocarbons | 0% mol | 0% mol | 0% mol |
| Composition Water | 0% mol | 0% mol | 0% mol |

Comparative Example 2

This comparative Example illustrates a plant according to the scheme of FIG. 6, a dehydrogenation plant of new or future construction according to the known art, operating according to the main functioning conditions indicated in Table 4.

The conversion of ethylbenzene is 68%, the ratio between steam and hydrocarbons is 1 kg/kg. These conditions represent the limit for the more evolved dehydrogenation catalysts available, which can be used in plants to be built in the future. In particular, the temperature of the steam leaving the first furnace of over 900° C. makes it necessary to adopt construction materials and solutions which are extremely expensive and potentially critical in terms of functioning reliability.

TABLE 4

(Referring to the scheme of FIG. 6).

| Stream | 1 | 2A | 2B | 2C | 2D | 3A |
|---|---|---|---|---|---|---|
| | Ethyl benzene feedstock | Steam in feeding | Steam from first furnace | Steam to second furnace | Steam to first reactor | Feed to first reactor |
| Flow-rate [kg/h] | 89700 | 57330 | 57330 | 57330 | 57330 | 147030 |
| T [° C.] | 489 | 369 | 907 | 654 | 880 | 625 |
| Composition Vent Gas | 0% by wt | 0% by wt | 0% by wt | 0% by wt | 0% by wt | 0% by wt |
| Composition Hydrocarbons | 82% by wt | 0% by wt | 0% by wt | 0% by wt | 0% by wt | 50% by wt |
| Composition Water | 18% by wt | 100% by wt | 100% by wt | 100% by wt | 100% by wt | 50% by wt |

| Stream | 3B | 3C | 3E | 3F | 4E | 5 |
|---|---|---|---|---|---|---|
| | Outlet First reactor | Feeding Second reactor | Outlet second reactor | Reaction product | Fumes from furnaces (3) | Natural Gas to furnaces |
| Flow-rate [kg/h] | 147030 | 147030 | 147030 | 147030 | 62000 | 3000 |
| T [° C.] | 535 | 632 | 565 | 165 | 150 | 25 |
| Composition Vent Gas | 5.4% mol | 5.4% mol | 10.3% mol | 10.3% mol | 83% mol | 100% mol |
| Composition Hydrocarbons | 13.6% mol | 13.6% mol | 13.1% mol | 13.1% mol | 0% mol | 0% mol |
| Composition Water | 81% mol | 81% mol | 76.6% mol | 76.6% mol | 17% mol | 0% mol |

Example 2

Example 2 illustrates the design of a new plant, which allows the maximum benefit to be drawn in terms of reduction in the vapour consumption deriving from the most recent catalysts. The reference Figure is FIG. 2 and the operating conditions are those indicated in Tables 5 and 6 with a conversion of ethylbenzene of 68% and the steam/hydrocarbon ratio is equal to 1 kg/kg.

The advantage derives from the possibility of reaching the same temperatures at the inlet of the reactors with lower temperatures of the heating circuits, in particular that of the vapour leaving the furnaces.

TABLE 5

(Referring to the scheme of FIG. 2).

| Stream | 1 | 1A | 2A | 2B | 2C | 2D |
|---|---|---|---|---|---|---|
| | Ethylbenzene feedstock | Ethylbenzene in feedstock | Steam In feeding | Steam from first furnace | Steam to second furnace | Steam to first reactor |
| Flow-rate [kg/h] | 89700 | 89700 | 57330 | 57330 | 57330 | 57330 |
| T [° C.] | 489 | 502 | 368 | 858 | 637 | 858 |
| Composition Vent Gas | 0% by wt | 0% by wt | 0% by wt | 0% by wt | 0% by wt | 0% by wt |
| Composition Hydrocarbons | 82% by wt | 82% by wt | 0% by wt | 0% by wt | 0% by wt | 0% by wt |
| Composition Water | 18% by wt | 18% by wt | 100% by wt | 100% by wt | 100% by wt | 100% by wt |

| Stream | 2E | 3A | 3B | 3C | 3D | 3E |
|---|---|---|---|---|---|---|
| | Steam to C1 | Feed First reactor | Outlet First reactor | Feed Ultra-heater | Feed second reactor | Outlet second reactor |
| Flow-rate [kg/h] | 744 | 147030 | 147030 | 147030 | 147030 | 147030 |

TABLE 5-continued (Referring to the scheme of FIG. 2).

| T [° C.] | 200 | 625 | 536 | 612 | 629 | 568 |
|---|---|---|---|---|---|---|
| Composition Vent Gas | 0% by wt | 0% by wt | 5.5%-mol | 5.5%-mol | 5.5%-mol | 8.9% mol |
| Composition Hydrocarbons | 0% by wt | 50% by wt | 11.0%-mol | 11.0%-mol | 11.0%-mol | 11.3% mol |
| Composition Water | 100% by wt | 50% by wt | 83.5% mol | 83.5% mol | 83.5% mol | 79.8% mol |

TABLE 6

(Referring to the scheme of FIG. 2).

| Stream | 3F | 4A | 4B | 4C | 4D | 4E |
|---|---|---|---|---|---|---|
|  | Product | Hot gases from V1 | Gas to ultra-heater | Gas from ultra-heater | Hot gases to furnaces | Fumes from furnaces |
| Flow-rate [kg/h] | 147030 | 70430 | 76000 | 76000 | 5570 | 63200 |
| T [° C.] | 162 | 720 | 790 | 747 | 720 | 150 |
| Composition Vent Gas | 8.9% mol | 70% vol | 70% vol | 70% vol | 70% vol | 82% vol |
| Composition Hydrocarbons | 11.3%-mol | 0% vol | 0% vol | 0% vol | 0% vol | 0% vol |
| Composition Water | 79.8% mol | 30% vol | 30% vol | 30% vol | 30% vol | 18% vol |

| Stream | 5 | 5A | 6A |
|---|---|---|---|
|  | Natural Gas to furnaces | Gas to C1 | Combustion air to C1 |
| Flow-rate [kg/h] | 2800 | 225 | 4600 |
| T [° C.] | 25 | 25 | 25 |
| Composition Vent Gas | 100% mol | 100% mol | 100% mol |
| Composition Hydrocarbons | 0% mol | 0% mol | 0% mol |
| Composition Water | 0% mol | 0% mol | 0% mol |

The invention claimed is:

1. An ethylbenzene dehydrogenation plant, comprising:
a reaction section comprising one adiabatic reactor or more than one adiabatic reactors positioned in series,
a steam circuit comprising a first steam heat exchange apparatus positioned downstream of the first adiabatic reaction device;
a heating equipment comprising the following apparatuses located in a heating circuit and in fluid communication with each other:
an ultra-heating apparatus,
a combustion device comprising a steam diffuser, one burner and a mixing apparatus, and
a ventilation device;
wherein the fumes produced in the combustion device are at least partially recirculated by means of the ventilation device through the heating circuit;
wherein the ultra-heating apparatus of the heating circuit is positioned between one adiabatic reactor and a subsequent adiabatic reactor, or is positioned on the feeding line of the feedstock to the first adiabatic reactor, or is positioned along the steam circuit.

2. The dehydrogenation plant according to claim 1, wherein the heating equipment comprises at least two ultra-heaters in series.

3. The dehydrogenation plant according to claim 2, wherein the first ultra-heater is positioned either upstream or downstream of said at least one first steam heat exchanger, and the subsequent ultra-heaters are positioned upstream of the ventilation device.

4. The plant according to claim 1, wherein the ventilation device is a centrifuge or axial ventilator, suitable for conveying high temperature gas.

5. The plant according to claim 1, wherein two or more ventilation devices are positioned in parallel downstream of a single ultra-heater and upstream of a single combustion device.

6. A process for the dehydrogenation of ethylbenzene to produce styrene in a plant according to claim 1, which comprises:
a. reacting a mixture of reagents comprising steam and ethylbenzene, in the presence of a catalyst, in one or more adiabatic reaction steps in series;
b. circulating steam in a steam circuit in which there is at least one first steam heat exchange apparatus, so that it transfers at least a part of its sensitive heat to the reagents or to the intermediate reaction products in the various reaction steps; and
c. heating a stream of fumes to a temperature lower than 800° C. and recirculating said fumes, formed during dehydrogenation processes of ethylbenzene to give styrene, so that they transfer their sensitive heat to the reagents, or to the intermediate reaction products generated during the various reaction steps, or to the steam necessary for effecting the dehydrogenation, or to a combination thereof.

7. The process according to claim 6, wherein the fumes are recirculated with a flow-rate ranging from 10,000 kg/h to 100,000 kg/h.

8. The process according to claim 7, wherein the fumes are recirculated with a flow-rate ranging from 50,000 kg/h to 80,000 kg/h.

9. The process according to claim 6, wherein the fumes are recirculated at a temperature ranging from 600° C. to 800° C.

10. The process according to claim 6, wherein the fumes contain vent gases, hydrocarbons and water and the water concentration ranges from 10% to 70% by volume.

11. The process according to claim 10, wherein the water concentration ranges from 15% to 45% by volume.

12. The process according to claim 9, wherein the fumes are maintained at a constant pressure during recirculation.

13. The process according to claim 6, effected in the dehydrogenation plant.

* * * * *